(12) United States Patent
Demuth et al.

(10) Patent No.: US 6,172,006 B1
(45) Date of Patent: Jan. 9, 2001

(54) FURYL-PYRIDONE COMPOUNDS, USEFUL AS FUNGICIDES AND OBTAINED FROM THE FUNGUS CLADOBOTRYUM

(75) Inventors: Helle Demuth, Copenhagen; Jens Breinholt, Bagsvaerd; Birgitte Rassing Romer, Copenhagen, all of (DK)

(73) Assignee: Novo Nordiskals, Bagsvaerd (DK)

( * ) Notice: Under 35 U.S.C. 154(b), the term of this patent shall be extended for 0 days.

(21) Appl. No.: 09/040,488

(22) Filed: Mar. 18, 1998

Related U.S. Application Data

(63) Continuation of application No. PCT/DK96/00398, filed on Sep. 19, 1996.

(30) Foreign Application Priority Data

Sep. 20, 1995 (DK) .................................................. 1050/95

(51) Int. Cl.⁷ ........................ A01N 43/40; C07D 491/48; C12P 17/18; C12N 1/14
(52) U.S. Cl. ........................ 504/246; 435/118; 435/254.1; 435/255.7; 435/911; 546/115
(58) Field of Search ..................................... 435/118, 911, 435/254.1, 255.7; 546/115; 514/302; 504/246

(56) References Cited

U.S. PATENT DOCUMENTS 5,714,595 * 2/1998 Viaud ................................... 514/300

OTHER PUBLICATIONS

Tezuka, et al., Chem. Pharm. Bull., vol. 42, No. 12, pp. 2612–2617 (1994).

* cited by examiner

*Primary Examiner*—Evelyn Mei Huang
(74) *Attorney, Agent, or Firm*—Elias J Lambiris; Valeta Gregg

(57) ABSTRACT

The invention relates to biologically active novel compounds having formula (I) as defined herein. Also disclosed are methods of preparing said compounds, fungicidal compositions comprising, as an active ingredient, these compounds, use of the compounds, and method of controlling fungi at loci infested or liable to be infested therewith.

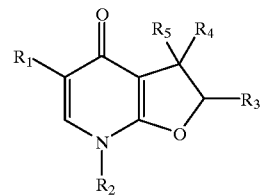

(I)

16 Claims, 2 Drawing Sheets

FURYL-PYRIDONE COMPOUNDS, USEFUL AS FUNGICIDES AND OBTAINED FROM THE FUNGUS CLADOBOTRYUM

CROSS-REFERENCE TO RELATED APPLICATIONS

This application is a continuation of PCT/DK96/00398 filed Sep. 19, 1996 and claims priority under 35 U.S.C. 119 of Danish application 1050195 filed Sep. 20, 1995, the contents of which are fully incorporated herein by reference.

FIELD OF THE INVENTION

The invention relates to biologically active compounds, methods for their production, and microorganisms capable of synthesizing such compounds.

The invention further relates to fungicidal compositions comprising said compounds and methods of controlling fungi by the use of such compositions.

Also contemplated is an isolated pure culture of a microorganism capable of producing said compounds.

BACKGROUND OF THE INVENTION

Synthetic chemical fungicides, pesticides, acaricides, preservatives etc. have been used for decades, in various fields, such as medicine, agriculture, forestry, horticulture, food industry etc. However, today it is realised that very often in general such chemicals, have a negative impact on the environment. Therefore, especially the search for biological agents such a as microbes and microbial metabolites, useful for controlling diseases and pests in valuable crops, has been a growing area of research during the last decade.

It is thus well known that microorganisms are capable of producing metabolites associated with interesting biological activities.

Strains of the fungal genus Cladobotryum have till now not been found capable of producing such useful compounds.

SUMMARY OF THE INVENTION

The present inventors have surprisingly succeeded in isolating and characterizing novel biologically active compounds from a fungus of the genus Cladobotryum.

The novel compounds have the generic formula I:

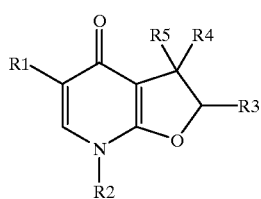

(I)

wherein
$R_1$ is aryl, such as phenyl, optionally mono- or plurisubstituted with alkyl with 1–6 carbon atoms, hydroxy, alkoxy, halogen, amino or a nitro group,
$R_2$ is hydrogen, straight or branched chain alkyl with 1–6 carbon atoms, straight or branched chain alkenyl with 2–6 carbon atoms, straight or branched chain alkynyl with 2–6 carbon atoms,
$R_3$ is hydrogen, straight or branched chain alkyl with 1–10 carbon atoms, straight or branched chain alkenyl with 2–10 carbon atoms, straight or branched chain alkynyl with 2–10 carbon atoms,
$R_4$ is hydrogen, straight or branched chain alkyl with 1–6 carbon atoms, straight or branched chain alkenyl with 2–6 carbon atoms, straight or branched chain alkynyl with 2–6 carbon atoms, and
$R_5$ is hydroxymethyl, formyl, carboxyl, or carboxyl ester with 1–6 carbon atoms.

In a preferred embodiment of compound with the formula I, $R_1$ is phenyl, $R_2$ is hydrogen, $R_3$ is 2-(2(E)-butenyl), $R_4$ is methyl, and $R_5$ is formyl resulting in a compound with the formula Ia.

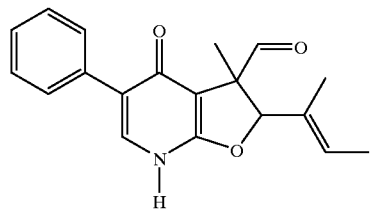

(Ia)

In another aspect, the invention relates to a method of preparing said compounds comprising
a) cultivating a microorganism capable of producing said compound in or on a suitable nutrient medium and under suitable conditions, and
b) recovering the compound from the biomass and/or the culture medium.

In an embodiment of the invention the method further comprises the step of c) chemically modifying the compound obtained in step b).

In a specific embodiment of the invention said microorganism is a fungus of the genus Cladobotryum, preferably of the is species *Cladobotryum varium*, especially of the strain *Cladobotryum varium* NN006437 (CBS 331.95) or a mutant thereof capable of producing a compound of the invention.

A third object of the invention is to provide a fungicidal composition comprising, as an active ingredient, said compound alone or in combination with one or more other fungicidal or pesticidal agents and/or growth regulators.

Also contemplated according to the invention is a method of controlling fungi at a locus infested or liable to be infested therewith, which comprises applying to said locus said compound or said composition of the invention.

Further the invention relates to the use of the novel compounds as a fungicide, preservative and/or additive for combating plant diseases, especially fungal attack or control fungi in timber, wood, cosmetics, paints, growth media, feeds and foods.

Lastly the invention relates to an isolated pure culture of the microorganism *Cladobotryum varium* NN0054922 (CBS 331.95) or a mutant thereof capable of producing a compound of the invention.

DETAILED DESCRIPTION OF THE INVENTION

Figure 1:
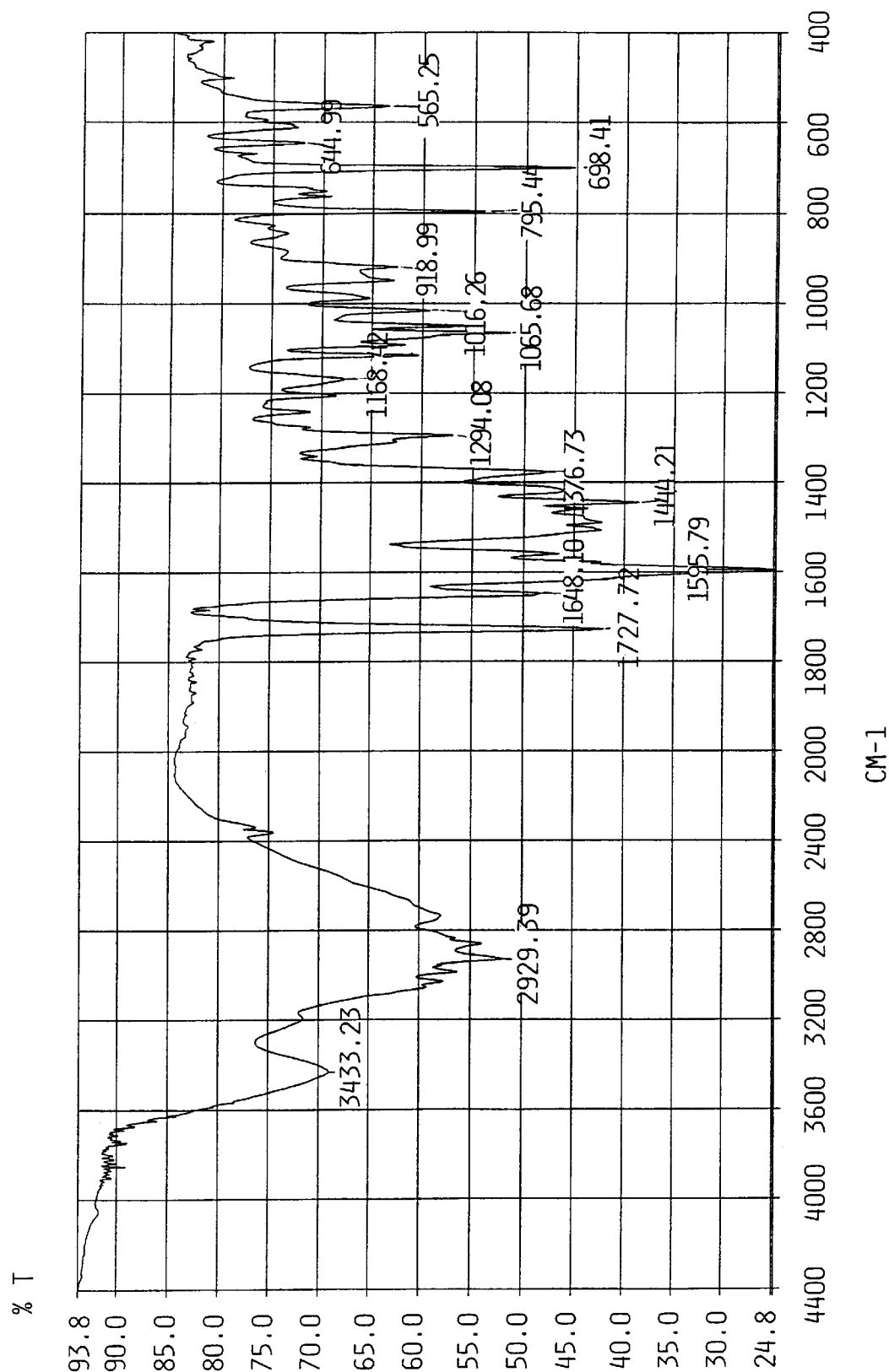
FIG. 1 shows the infra red spectrum (IR-spectrum) of the compound with the formula Ia.

As indicated above the invention relates, in its first aspect, to novel compounds having the generic formula I:

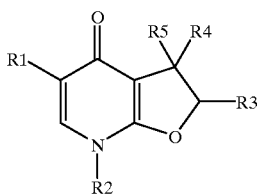

(I)

wherein $R_1$ is aryl, such as phenyl, optionally mono- or plurisubstituted with alkyl with 1–6 carbon atoms, hydroxy, alkoxy, halogen, amino or a nitro group, $R_2$ is hydrogen, straight or branched chain alkyl with 1–6 carbon atoms, straight or branched chain alkenyl with 2–6 carbon atoms, straight or branched chain alkynyl with 2–6 carbon atoms, $R_3$ is hydrogen, straight or branched chain alkyl with 1–10 carbon atoms, straight or branched chain alkenyl with 2–10 carbon atoms, straight or branched chain alkynyl with 2–10 carbon atoms, $R_4$ is hydrogen, straight or branched chain alkyl with 1–6 carbon atoms, straight or branched chain alkenyl with 2–6 carbon atoms, straight or branched chain alkynyl with 2–6 carbon atoms, and $R_5$ is hydroxymethyl, formyl, carboxyl, or carboxyl ester with 1–6 carbon atoms.

In connection with the compounds of the present invention having the formula I, the terms "alkyl with 1–10 carbon atoms" and "alkyl with 1–6 carbon atoms" are intended to include methyl, ethyl, propyl, butyl, pentyl, hexyl etc. straight, branched or cyclic where appropriate.

The terms "alkenyl with 2–10 carbon atoms" and "alkenyl with 2–6 carbon atoms" are intended to include ethenyl, propenyl, butenyl, pentenyl, hexenyl etc. straight, branched or cyclic where appropriate. Also polyenyl (dienyl, trienyl etc.) is intended to be included in the term.

The terms "alkynyl with 2–10 carbon atoms" and "alkynyl with 2–6 carbon atoms" are intended to include ethynyl, propynyl, butynyl pentynyl, hexynyl etc. straight, branched or cyclic where appropriate. Also polyynyl (diynyl, triynyl etc.) is intended to be included in the term.

The term "aryl" is intended to include aromatic radicals like phenyl, naphtyl, phenantryl etc. and hetero aromatic radicals like furanyl, thiophenyl, pyridinyl, imidazolyl, oxazolyl etc.

The term "plurisubstituted" covers di-, tri-, tetra- or higher substitution.

In a preferred embodiment of compound with the formula I, $R_1$ is phenyl, $R_2$ is hydrogen, $R_3$ is 2-(2(E)-butenyl), $R_4$ is methyl, and $R_5$ is formyl resulting in a compound with the formula Ia.

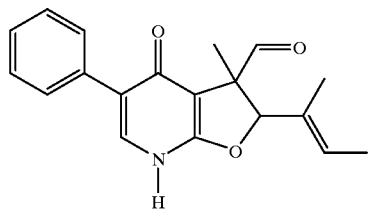

(Ia)

Another object of the invention is to provide a method of preparing compounds with the formula I, comprising a) cultivating a microorganism capable of producing said compound in or on a suitable nutrient medium and under suitable conditions, and b) recovering the compound from the biomass and/or the culture medium.

Also contemplated according to the invention are methods which further comprise a step c) of chemically modifying the compound obtained in step b).

In a specific embodiment said microorganism is a fungus, preferably of the genus Cladobotryum especially of the species *Cladobotryum varium*, in particular the strain thereof identified by the deposition number CBS 331.95, or a mutant thereof capable is of producing a compound of the invention.

An isolate of the fungus *Cladobotryum varium* NN006437 (CBS 331.95) has been deposited with the Centraalbureau voor Schimmel-cultures, P.O. Box 273, 3740 AG Baarn, The Netherlands, for the purposes of patent procedure on the date indicated below. CBS being an international depository under the Budapest Treaty affords permanence of the deposit in accordance with rule 9 of said treaty.

Deposit date : 12 May 1995
Depositor's ref.: NN006437
CBS designation : CBS No. 331.95

Further the isolate of the fungus *Cladobotryum varium* NN006437 (CBS 331.95) has been deposited under conditions that assure that access to the isolated fungus will be available during the pendency of this patent application to one determined by the commissioner of Patents and Trademarks to be entitled thereto under 37 C.F.R. §1.14 and 35 U.S.C §122. The deposit represents a substantially pure culture of the isolated fungus. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

A suitable nutrient medium is one which comprises the micro- and macronutrients required to obtain a satisfactory growth of the microorganism in question and at the same time give rise to a production of the compound of the invention when subjected to suitable cultivation conditions.

Normally, a suitable nutrient medium contain sources of carbon and nitrogen assimilable by the microorganism and normally a low level of inorganic salts. In addition, the nutrient medium may contain traces of metals and other components necessary for the growth of the microorganisms and the production of the desired compound. Such other components may be in sufficient concentrations in the complex sources of carbon and nitrogen, typically used as nutrient sources, but can, of course, be added separately to the medium if desired.

The conditions under which the microorganism is cultivated may be chosen so as to optimize the production of secondary metabolites therefrom. The optimization of the production of secondary metabolites may be performed by methods known in the art, such as methods based on submerged fermentation (batch fermentation, fed-batch fermentation or continuous fermentation), or on surface culture on a liquid, solid or semi solid media.

When the compound is produced in submerged fermentation it may be contained in the biomass or may alternatively be excreted into the culture medium, fully or partially, depending on the microorganism in question.

The recovery of the compound of the invention from the biomass and/or culture medium produced in accordance with step a) above may be performed by any suitable technique useful for the microorganism in question. The recovery of the compound comprises harvesting the mycelium, e.g. by filtration and/or centrifugation, and subsequently isolating the compound from either the biomass and/or the centrifugate/filtrate. When fermented on solid media the compound may be recovered by direct extraction of the whole culture. Suitable methods for isolating the compound includes extraction of whole culture, the biomass, or filtrate/centrifugate using a suitable solvent such as polar solvents like methanol, ethanol, ethyl acetate, or acetone, and solid phase extraction using a hydrophobic resin, an example of which is XAD-8 (Rohm and Haas Co.). Further purification may be accomplished by chromatography and/or crystallisation.

In order to improve certain properties of the metabolite such as its solubility in aqueous media, its hydrophobicity, hydrophilicity, stability, specificity, toxicity, target spectrum, potency, UV or heat resistance or the sensitivity of the compound to pH variations, etc. as well as membrane permeability and translocation of the compound in the host plant to which it is applied, it may be advantageous to subject the isolated natural metabolite to a chemical modification. Alternatively, modification may be achieved by feeding suitable precursors to the medium in which the microorganism producing the compound is. cultured to obtain production of the derivative. Furthermore, derivatives may be produced by chemical synthesis using the natural metabolite as a lead structure. The compounds produced by such modifications may either belong to the group of compounds having the general formula I or may be different from these compounds.

An example of the production of compounds with the formula I is given below. The example describes the production of the specific compound with the formula Ia, from a culture of the deposited microorganism (CBS 331.95) of the invention.

While it is contemplated that compounds of the invention having formula I may be prepared by the general method outlined above, i.e. from a microorganism capable of producing such compounds, compounds of the invention may advantageously be prepared from the compound with the formula Ia using a synthetic process.

It is also contemplated that compounds, according to the invention, may be produced entirely by well known chemical synthetic processes using available starting materials.

Still another object of the invention is to provide a fungicidal composition comprising, as an active ingredient, said novel compound with the formula I.

In an embodiment of the invention said fungicidal composition comprises one of said compounds in an amount of from 0.001 µg/ml to 100 mg/ml. Alternatively, the active ingredient may be a fungus of a species belonging to the genus Cladobotryum capable of producing said novel compound, preferably of the species *Cladobotryum varium*, especially a strain of the *Cladobotryum varium* NN006437 (CBS No. 331.95) or a mutant thereof capable of producing said compound of the invention.

In this context it was specifically found that organic extracts of fermentations of the fungus, especially of the strain *Cladobotryum varium* NN006437 (CBS 331.95) inhibited the growth of various plant pathogenic fungi. The principle responsible for the observed activity was isolated and characterized spectroscopically, chemically and biologically as described below.

Fungicidal compositions according to the invention, exhibiting fungicidal and optionally antibacterial activity, having compounds of the invention as an active ingredient, may for agronomical and/or horticultural applications be formulated by mixing the active principle with suitable inert and compatible carriers or diluents to obtain a composition of the type generally used in agricultural compositions, examples of which are further discussed below.

The diluent or carrier in the composition of the invention may be a solid or a liquid conventionally used for the purpose. As solid carriers bentonite, diatomaceous earth, apatite, gypsum, talc, pyrophyllite, vermiculite, ground shells, and clay may be mentioned.

In order to obtain a homogeneous and/or stable formulation, a surface-active agent may be associated with the diluent or carrier. The surface-active agent may, for instance, be a dispersing agent, an emulsifying agent or a wetting agent, examples of which are anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g. butylnaphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate of dioctyl succinate. Non-ionic agents include condensation products of fatty acid esters, fatty alcohols, fatty acid amides or fatty-alkyl- of alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols.

Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The composition of the invention can the in any form known in the art for the formulation of agrochemicals, for example, an emulsifiable concentrate, a concentrated emulsion, a multiple emulsion, an aqueous emulsion, a solution, a dispersion, a suspension concentrate, a release formulation (including a slow release formulation), a seed dressing, a granular formulation, a water soluble powder, a wettable powder, a dusting powder, a dispersible powder, an alginate, a xanthan gum and/or an aerosol. Moreover, it can be in a suitable form for direct application or as a concentrate or primary composition which requires dilution with a suitable quantity of water or other diluent before application.

An emulsifiable concentrate comprises the active ingredient dissolved in a water-immiscible solvent which is formed into an emulsion with water in the presence of an emulsifying agent. Another suitable concentrate is a flowable suspension concentrate which is formed by grinding the active ingredient with water or other liquid, a wetting agent and a suspending agent.

A dusting powder comprises the active ingredient intimately mixed and ground with a solid pulverulent diluent, for example, kaolin. A granular solid comprises the active ingredient associated with similar diluents to those which may be employed in dusting powders, but the mixture is granulated by known methods. Alternatively it comprises the active ingredient absorbed or adsorbed on a pre-granular diluent for example, Fuller's earth, attapulgite or limestone grit. Wettable powders, granules or grains usually comprise the active ingredient in admixture with a suitable surfactant and an inert powder diluent such as china clay.

Depending on the circumstances such as the crop wherein fungi are to be controlled, the environmental conditions or other factors, a composition of the invention in addition to said fungicidally active compounds of the invention may also contain other active ingredients, e.g. fungicides, pesticides, herbicides, insecticides, nematocides or acaricides, or plant nutrients or fertilizers.

Examples of fungicides which can be combined with the active compounds of the invention include especially ergosterol biosynthesis inhibitors ("EBIs"). These are generally imidazole or triazole derivatives and examples include those known by the common names prochloraz, triadimefon, propiconazole, diclobutrazol, triadiminol, flusilazole, flutriafol, myclobutanil, penconazole, quinconazole, imazalil and diniconazole. Examples of non azole EBis include nuarimol, fenarimol, fenpropimorph, tridemorph, fenpropidine and dimethomorph.

Further fungicides which can be combined with compounds of the invention include:
Dithiocarbamates, e.g. thiram, maneb, zineb and mancozeb;
Phatalimides, e.g. captan, folpet and captafol;
Carboxines, e.g. carboxin and oxycarboxin;
Benzimidazoles, e.g. benomyl, carbendazim and fuberidazole;
Carbamates, e.g. prothiocarb and propamocarb;
Isoxazoles, e.g. hymexazol;
Cyanoacetamides, e.g. cymoxanil;
Ethylphosphonates, e.g. fosetylaluminium;
Phenylamides, e.g. furalaxyl, metalaxyl, benalaxyl, ofurace, cyprofuram and oxandixyl;
Dicarboximides, e.g. procymidone, iprodione and vinclozolin;
Organophosphorous fungicides, e.g. pyrazophos, triamiphos, ditalimfos and tolcofosmethyl;
Aromatic hydrocarbon fungicides, e.g. quintozene, dichloren, and diphenyl;
Pyrimidines, e.g. pyrimethanil, and Dinitroanilies, e.g. fluazinam.

The concentration of the active compounds of the invention described herein in the compositions of the invention may vary within a wide range depending on the type of formulation and the field of application.

In order to provide the antifungal composition of the invention with a satisfactory activity, the active compound should normally be present in an amount from 0.001 $\mu$g/ml to 100 mg/ml, such as 0.1 $\mu$g/ml to 5 mg/ml.

The concentration of the biologically active compounds of the invention in the compositions of the present invention when used alone or in combination with a conventional fungicide, as applied to plants is preferably within the range from about 0.001 to about 30 per cent by weight, especially 0.01 to 3.0 per cent by weight, although it may vary more widely and be, for instance, within the range from about 5 to about 95 per cent by weight of the composition.

The concentration of the other fungicidally active ingredient in the mixed composition of the present invention, as applied to plants is preferably within the range of 0.001 to 50 per cent by weight, especially 0.01 to 10 per cent by weight, although it can vary widely and can be, for example, from 5 to 80 per cent by weight of the composition.

The composition according to the invention may also comprise compounds which contributes to various functions, such as protection of the fungicidal properties of the active components from sun, or UV damage.

Examples of preferred UV protectants are lignins or lignin derivatives, which are readily available by-product of the pulp and paper industry, alone or combined with sugar alcohols as described in the pending international patent application no. PCT/US95/01760 (Entotech, Inc.).

Examples of suitable lignins comprise lignin sulfulfonate and salts thereof (e.g. Na, K, Ca, and Mg salts), oxylignins and salts thereof, lignin liquors, Kraft lignins and derivatives thereof and low and high lignins.

An "effective amount" of lignin refers to an amount which when combined with an effective amount of sugar alcohol, under normal sun conditions, increases the UV protection of the composition at least 25%, and preferably at least 50%, relative to the protection provided by lignin alone in the same composition. The amount of lignin in the composition is at least 2% w/w, up to about 95% w/w, and preferably at least about 5% w/w, most preferably at least about 15% w/w, up to about 50% w/w.

The sugar alcohols have the formula $CH_2OH(CHOH)_nCH_2OH$, wherein n is an integer from 2 to 5. Among the sugar alcohols useful for this purpose are sorbitol, mannitol and xylitol.

An "effective amount" of a sugar alcohol is that amount, which in combination with a given amount of lignin, will enhance the UV protective properties of lignin at least 25%, and preferably at least 50%, relative to lignin alone in the same composition. A preferred concentration of the sugar alcohol in the composition is at least 4% w/w, up to about 95% w/w, and preferably at least about 10% w/w, up to about 35% w/w.

In order to achieve maximum efficacy, the formulation containing a fungicide or a pesticide must first be deposited directly on the plants to be treated, and then must adhere to and remain active on the surface to which it is applied. To achieve this goal, the UV protecting components may be supplemented with other components.

Therefore the composition according to the invention may further advantageously comprise at least one agent which is capable of enhancing deposition (hereinafter, "deposition agent") of the composition, i.e., a component which will assist in keeping it from drifting from the target area as it is being applied (e.g. as it is sprayed from a plane), or from being blown away from the plant once it has been deposited. The deposition agent thus should be a component which has sufficient density to prevent random dispersal.

Any animal or vegetable protein is suitable for this purpose, in dry or in liquid form. Examples of useful sources of protein which can be conveniently and economically added to the formulation are soy protein, potato protein, soy flour, potato flour, fish meal, bone meal, yeast extract, blood meal and the like.

However, protein is not the only material which can be used in this manner. Alternative deposition agents include modified cellulose (e.g. carboxymethylcellulose), botanicals (e.g. grain flours, ground plant parts), natural earths (talc, vermiticulite, diatomaceous earth), natural clays (e.g. attapulgite, bentonite, kaolinite, montmorillonite), or synthetic (e.g. Laponite).

When utilized, the deposition agent preferably constitutes at least about 1% w/w up to about 50w/w, more preferably at least 2% w/w up to about 20% w/w.

Retention of the composition can be aided by inclusion of an adherent component. To this end, one or more polyhydric alcohols are added to the composition. This component can serve a number of functions. First, it functions as an adherent which permits the composition to stick to the plant surface. In addition, these components serve as a humectant, to attract moisture to the composition in situ. Such components also can be useful in preventing freezing of the composition, thereby protecting the activity of the fungicidal component.

The alcohol component can be chosen from one or more of the following: ethylene glycol, propylene glycol, dipropylene glycol, glycerol, butylene glycols, pentylene glycols, hexylene glycols; the sugar alcohol component may also contribute to this function, but it is desirable to add a second polyhydric alcohol to the composition. Overall, the second polyhydric alcohol component of the composition, if present, should comprise from about 1 to about 20% w/w of the total composition.

The invention also relates to the use of these active ingredients alone or in combination with one or more other fungicidal or pesticidal agents and/or growth regulators for controlling fungi in agriculture, forestry, horticulture etc.

In a further aspect the invention relates to a method of controlling fungi at a locus infested or liable to be infested therewith, which comprises applying to said locus a compound or a composition of the invention as defined above.

In an embodiment of the invention said compound or composition is applied to a locus selected from the group consisting of plants, timber, wood, cosmetics, feeds and foods.

In relation to plants the compounds of the invention can be used on both monocotyledons and dicotyledons. Specific examples are members of the *Graminea genera,* such as Poacea; Leguminosea; vegetables; fruits; etc.

Specifically the compounds of the invention can be used for controlling plant pathogenic fungi on vegetables, such as potatoes, turnips, beets, etc.

The compounds of the invention can be also be used for controlling plant pathogenic fungi on fruits, such as apples and pears, and citrus fruits, such as oranges and lemons.

Specifically the compounds of the invention are especially useful for controlling plant pathogenic fungi on cereals, such as wheat, barley, oats, corn, and rice.

Compounds of the invention have been found to be particularly potent towards fungi belonging to the class Oomyceta, especially plant pathogenic fungi belonging to the class Oomyceta.

Examples of fungi belonging to the class Oomyceta which has been found to be sensitive to compounds of the invention are fungi of the genera Phytophthora, especially *P. cryptogea* and *P. nicotianea,* or Pythium, especially *P. ultimum* and P. Type F.

Compounds of the formula Ia have been found to exhibit some activity towards imperfect fungi such as Pyricularia, especially *Pyricularia oryzae*, and Fusarium, especially *Fusarium oxysporum* or Ascomyceta such as Venturia, especially *Venturia inaeqalis.*

In connection with the method of the invention for controlling fungi, the composition may for agronomical or horticultural uses be applied to a region to be treated either directly to the soil as a pre-emergence treatment or to the foliage or fruits of the plants as a pre- and/or post-emergence treatment. Depending on the crop and circumstances the treatment may be postponed until seeds or fruits appear on the plants, wherein fungi are to be controlled. Sometimes, it is practicable to treat the roots of a plant before or during planting, for example by dipping the roots in a suitable liquid or solid composition.

The active preparation or the compositions of the invention can be applied directly to the plant by, for example, spraying or dusting either at the time when the fungus has begun to appear on the plant or before the appearance of fungus as a protective is measure. In both such cases the preferred mode of application is by foliar spraying.

It is generally important to obtain good control of fungi in the early stages of plant growth as this is the time when the plant can be most severely damaged. The spray or dust can conveniently contain a pre-or post-emergence herbicide if this is thought necessary. When the active preparation of the invention is applied directly to the plant a suitable rate of application is from 0.001 to 50 kg per hectare of active compound, preferably from 0.05 to 5 kg per hectare of active compound.

In the method of the invention the active preparation of the invention alone or in combination with a conventional biocide can also be applied to seeds or other habitats. Thus the preparation can be applied directly to the soil before, at or after drilling so that the presence of active ingredient in the soil can control the growth of fungi which may attack seeds.

The compositions may be applied in amounts corresponding to from about 1 g to about 50 kg biologically active compound per hectare.

When the soil is treated directly the active preparation alone or in a mixture with the conventional biocide can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 0.01 to 50 kg of active compound per hectare, more preferably from 0.05 to 5 kg of active compound per hectare.

Although the present invention has been described in detail in connection with controlling fungi on plants, it is also anticipated that the active compounds of the invention, may be used for controlling fungi in mammals, including humans; for the preservation of cosmetics; for the preservation for wood by adding said compounds to wood preservation and/or impregnation compositions; for the preservation of food or feed by adding the compounds directly to the food or feed or to the containers in which it is present; and for the preservation of cosmetics. Also, the active compounds of the invention may be useful as a fungicide and preservant in paints—both to prevent growth in the paint during storage, and growth on the painted object such as the plastered surface of a house—and as an additive to growth media, e.g. for cultivation of certain bacteria or yeast.

A final aspect of the invention is to provide an isolated pure culture of the microorganism *Cladobotryum varium* NN006437 (CBS 331.95) or a mutant thereof capable of producing a compound of the invention.

EXAMPLES

Example 1

Fermentation

Cultivation of the strain

*Cladobotryum varium* (CBS 331.95) was propagated on petri dishes (9 cm-diameter) each containing 20 ml of potato dextrose agar (PDA, 39 g/L) for 7 days at 26° C.

Metabolite Production

The metabolite of formula Ia was produced on malt extract agar (MEA: malt extract 20–40 g/L; peptone; 1 g/L; glucose, 20 g/L). Inoculation of the MEA-plates, each containing 20 ml of the MEA-medium, was performed by transferring agar plugs with mycelial growth from 7 days old PDA-plates. The fermentation on MEA was conducted for 12–14 days at 26° C.

Example 2

Isolation of Compound having Formula Ia

Extraction: The contents of 94 petri dishes were extracted under mechanical stirring with 2.5 L of EtOH for 30 min. The solids were filtered off and extracted with a second 2.5 L portion of EtOH for two hours. After filtration the combined EtOH-extracts were evaporated in vacuo. The residue was dissolved in water (500 ml) and extracted twice with EtOAc (2×500 ml). The combined organic extracts were dried and the solvent evaporated. Purification: The EtOAc-extract dissolved in $CH_2Cl_2$-MeOH (9:1) was in four portions subjected to silica gel column chromatography is (Merck Lobar, size B, eluted at a flow rate of 7.5 ml/min with a linear gradient from 10% tert-bytylmethyl ether (BME) in heptane to 100% BME over 30 min, isocratically 100% BME for 5 min, and form 100% BME to 100% MeOH over 10 min; UV detection at 240 nm). The peak eluting at ~40 min was collected to yield almost pure BA352. The compound was further purified by crystallisation from MeOOH.

Example 3

Characterization of Compound Ia

A culture of the strain *Cladobotyum varium* NN006437 (CBS 331.95) was cultivated, incubated, fermented, isolated and purified as described above.

Figure 2:
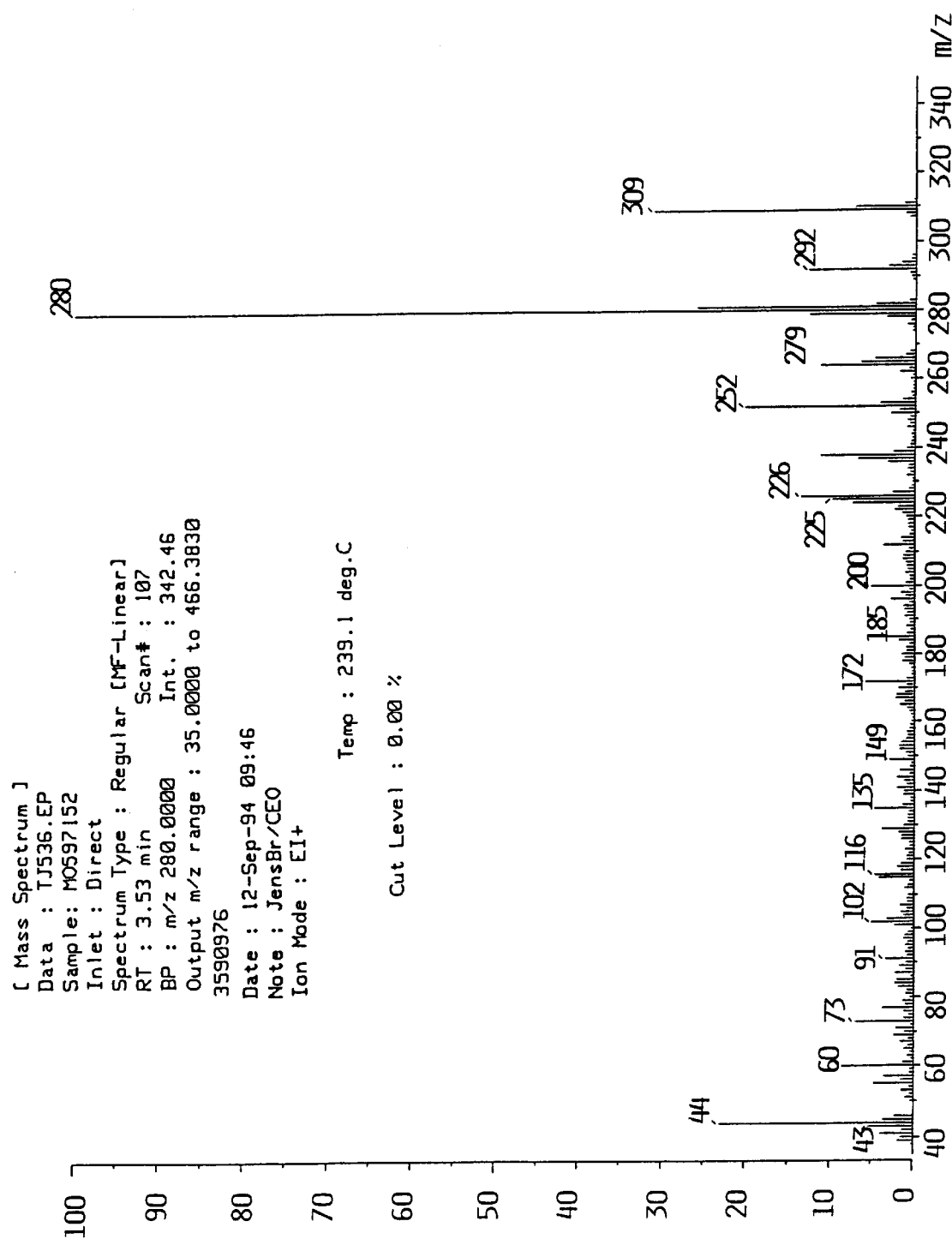
FIG. 2 shows the EIMS spectrum of the compound with the formula Ia.

The materials obtained was found to have the following physical and spectroscopic properties:

| | Compound Ia |
|---|---|
| Appearance: | Colourless needles |
| Melting point: | 198–199° C. |
| Optical rotation $[\alpha]_D$: | 46° (c = 0.7 MeOH) |
| HR-EIMS: | |
| Found: | 309.1367 ($M^+$) |
| Calc: | 309.1364 ($C_{19}H_{19}NO_3$) |
| IR spectrum: | FIG. 1 |
| EIMS-spectrum: | FIG. 2 |
| $^1$H-NMR spectra: | Table 1 |
| $^{13}$C-NMR spectra: | Table 1 |

TABLE 1

$^1$H and $^{13}$C NMR data for Ia. Numbering according to the formula Ib below. δ-values in ppm relative to solvent peaks at 77.0 ($^{13}$C) and 7.27 ($^1$H).

| Position | $^{13}$C | $^1$H |
|---|---|---|
| 2 | 167.6 | |
| 3 | 105.6 | |
| 4 | 159.5 | |
| 5 | 121.9 | |
| 6 | 148.4[a] | 7.87(1H, s) |
| 7 | 57.9 | |
| 8 | 93.8 | 4.97(1H, s) |
| 9 | 130.4 | |
| 10 | 126.1 | 5.84(1H, q, J=6.8 Hz) |
| 11 | 13.1 | 1.70(1H, d, J=6.8 Hz) |
| 12 | 133.9 | |
| 13/13' | 129.3 | 7.48(m) |
| 14/14' | 128.9 | 7.48(m) |
| 15 | 127.8 | 7.38(m) |
| 16 | 202.7 | 9.71(1H, s) |
| 17 | 21.7 | 1.64(3H, s) |
| 18 | 12.2 | 1.55(3H, s, br) |

[a] $^1J_{CH}$=175 Hz)

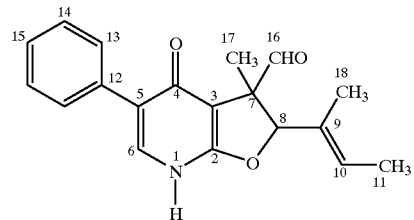

Ib

These obtained data provide evidence for the structure of compound Ia.

Fungicidal Activity

Agar diffusion assay

The compound has been found to have an in vitro inhibitory effect on the growth of fungi belonging to the class Oomyceta.

It was found to be particularly potent towards:

Class Oomyceta

Phytophthora, especially *P. cryptogea* and *P. nicotianae*

Pythium, especially *P. ultimum* and P. Type F

It was found to have some activity towards:

Class Ascomycota

*Venturia inaequalis*

Imperfect fungi

*Pyricularia oryzae* (sexual stage *Magnaporthe grisea*).

*Fusarium oxysporum*

In the inhibition assays the test organisms were embedded in agar media. Small wells were punched in the agar and 15 μl sample was applied to the wells. Inhibition zones were scored after incubation in dark for 2 days at 26° C.

Table 2 shows the activity observed when applying a 1000 ppm (1 mg/ml) and 100 ppm (0.1 mg/ml) solution of compound Ia in EtOH.

TABLE 2

| Test organism | Ia 1000 ppm Activity −/+ | Ia 100 ppm Activity −/+ |
|---|---|---|
| *Pyricularia oryzae* | + | − |
| *Venturia inaequalis* | ++ | − |
| *Fusarium oxysporum* | ++ | − |
| *Phytophthora cryptogea* | ++ | ++ |
| *Phytophthora nicotianae* | +++ | ++ |
| *Pythium ultimum* | ++++ | +++ |
| *Pythium Type F* | ++++ | +++ |
| *Aphanomyces euteiches* | + | − |
| Bacterial targets | | |
| *Bacillus subtilis* (G+) | +++ | − |
| *Pseudomonas aeruginosa* (G−) | − | − |

+ <10 mm
++ 11–20 mm
+++ 21–30 mm
++++ 31–49 mm

The present invention is not to be limited in scope by the above examples since they are only intended as illustrations of the invention. Indeed, various modifications of the invention in addition to those shown and described herein will from the foregoing description become apparent to those skilled in the art. Such modifications are intended to fall within the scope of the appended claims.

What is claimed is:

1. A compound of the formula Ia

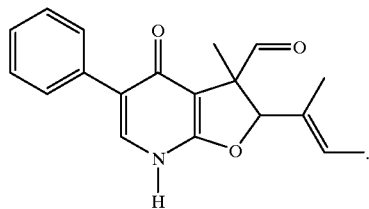

(Ia)

2. A method of preparing the compound of claim 1, comprising:
   a) cultivating a fungus which is Cladobotyrum under conditions wherein the compound is produced;
   b) recovering the compound from the biomass and/or the culture medium; and optionally
   c) chemically modifying the compound obtained in step b).

3. A fungicidal composition comprising, as an active ingredient, the compound of claim 2 together with one or more carriers or diluents.

4. The fungicidal composition of claim 3, wherein said compound is present in an amount of from 0.001 μg/ml to 100 mg/ml.

5. The fungicidal composition of claim 3, wherein the compound is produced by *Cladobotryum varium* NN006437 (CBS 331.95).

6. The fungicidal composition of claim 3, further comprising one or more fungicidal or pesticidal agents and/or growth regulators.

7. The fungicidal composition of claim 6, wherein the agent or growth regulator is present in an amount of 0.001% to 50% (w/w) by weight.

8. The fungicidal composition of claim 3, further comprising adjuvants selected from the group consisting of UV protective compounds, retention compounds, and surface active compounds.

9. A method of controlling fungi at a locus infested or liable to be infested therewith, comprising applying to the locus the compound of claim 1.

10. The method of claim 9, wherein the locus is selected from the group consisting of plants, timber, wood, cosmetics, feeds and foods.

11. The method according to claim 9, wherein the fungus to be controlled is a plant pathogenic fungus.

12. The method of claim 11, wherein the fungus to be controlled belongs to the genera Phytophthora, Venturia, Pyricularia, or Fusarium.

13. The method of claim 2, wherein the Cladebotryum fungus is of the species *Cladobotryum varium*.

14. The fungicidal composition of claim 7, wherein the other active agent is present in an amount of 0.01% to 10% (w/w).

15. The method of claim 11, wherein the plant pathogenic fungus belongs to the class Oomyceta.

16. The method of claim 12, wherein the fungus to be controlled belongs to the genera *Phytophthora cryptogea, Phytophthora nicotianae, Pythium ultimum,* Pythium Type F, *Venturia inaequalis, Pyricularia oryzae* or *Fusarium oxysporum.*

* * * * *